(12) United States Patent
Bak et al.

(10) Patent No.: US 6,392,128 B1
(45) Date of Patent: *May 21, 2002

(54) *AECHMEA FASCIATA* PLANT NAMED 'PRIMERA'

(75) Inventors: Elly Bak, Rijsenhout; Nicolaas D. M. Steur, Oude Niedorp, both of (NL)

(73) Assignee: Corn. Bak B.V., Assendelft (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/343,213

(22) Filed: Jun. 30, 1999

Related U.S. Application Data

(63) Continuation-in-part of application No. 09/244,097, filed on Feb. 4, 1999.

(51) Int. Cl.$^7$ .............................. A01H 1/00; A01H 5/00
(52) U.S. Cl. ...................... 800/323; 800/260; 800/298; Plt./371
(58) Field of Search .................. Plt./371; 800/298, 800/323, 260

(56) References Cited

FOREIGN PATENT DOCUMENTS

| EP | 98/1095 | 7/1998 |
|---|---|---|
| EP | 4712 | 6/1999 |

OTHER PUBLICATIONS

UPOV–ROM GTITM Computer Database 2000/2, GTI Jouve Retrieval Software, Citations for Aechmea named 'Primera', 2000.*

Benzing, David H., "The Biology of the Bromeliads", Mad River Press, Eureka, CA, pp 1–287 (1980).

Rauh et al., "Bromelien Tillandsien und andere kulturwurdige Bromelien", Eugen Ulmer, Stuttgart, Germany, pp 7–68 (1981).

Zimmer et al., "Bromelien Botanik und Anzucht ausgewahlter Arten", Parey, Berlin; Hamburg, Germany, pp 9–94 (1986).

* cited by examiner

*Primary Examiner*—Bruce R. Campell
*Assistant Examiner*—Cynthia Collins
(74) *Attorney, Agent, or Firm*—Foley & Lardner

(57) ABSTRACT

A new cultivar of *Aechmea fasciata* named 'Primera' characterized by its primary bract color of RHS 66D; broadly obovate leaves which are spineless with a dark greyed-green color (RHS 189A) and transverse white bands and patches.

5 Claims, 1 Drawing Sheet

(1 of 1 Drawing Sheet(s) Filed in Color)

AECHMEA FASCIATA PLANT NAMED 'PRIMERA'

This is a continuation-in-part application of U.S. patent application Ser. No. 09/244,097, filed Feb. 4, 1999.

FIELD OF INVENTION

The present invention relates to a new and distinct cultivar of *Aechnea fasciata*, a genus within the family of Bromeliaceae, hereinafter referred to by the cultivar name 'Primera'. The present invention relates to seeds which are *Aechmea fasciata* cultivar 'Primera', as well as plants and plant parts produced from these seeds which have all the morphological and physiological characteristics of the *Aechmea fasciata* cultivar 'Primera', as well as to methods for producing these seeds and plants.

BACKGROUND OF THE INVENTION

Aechmea comprises a genus of more than 168 species of evergreen perennials suitable for cultivation in the home or in the greenhouse. Aechmea may be terrestrial or epiphytic. For the most part, the species vary in diameter from 12 to 18 inches to 3 or 4 feet and have rosettes of spiny-edged leaves.

Flowers and bracts of Aechmea frequently have brilliant colors and may last for several months. The range of colors for Aechmea is generally from the yellow through orange but may also include pink, orange, red and red-purple. Tubular, three-petalled flowers may also appear but are usually short-lived.

Aechmea may be advantageously grown as pot plants for greenhouse or home use. Typically, the plants are shaded from direct sunlight during cultivation. The central, vase-like part of the leaf rosette is normally filled with water, Aechmea is native to tropical America. Aechmea leaves are usually formed as basal rosettes which are entire and in several vertical ranks. Aechmea has terminal spikes or panicles which are often bracted with petals united in a tube longer than the calyx.

Asexual propagation of Aechmea is frequently done through the use of tissue culture practices. Propagation can also be from offshoots which can be detached from the mother plant and grown in an appropriate soil or bark mixture. Methods for cultivating and crossing of Aechmea are well known. For a detailed description, reference is made to the following publications, the disclosures of which are incorporated herein by reference: Benzing, David H., THE BIOLOGY OF THE BROMELIADS, Mad River Press, Inc., Eureka (1980); Zimmer, Karl, BROMELIEN, Verlag Paul Parey, Berlin (1986); and Rauh, Werner, BROMELIEN, Verlag Eugen Ulmer, Stuttgart (1981).

An Aechmea inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect to their morphological and physiological characteristics.

A need exists for a greater variety of Aechmea cultivars with attractive ornamental features. Additionally, a need exists for additional Aechmea hybrid cultivars that can be easily propagated by seed.

SUMMARY OF THE INVENTION

These and other objectives have been achieved in accordance with the present invention which provides a new cultivar 'Primera' that is a product of a planned breeding program undertaken by the inventors in Assendelft, The Netherlands. The male or pollen parent was a selection of *Aechmea fasciata* identified by Code No. 95265026. The female or seed parent was a selection of *Aechmea fasciata* identified by Code No. 95265271.

Both parents have a sufficient degree of homozygosity such that the progeny of the cross are genetically and phenotypically uniform. The variety 'Primera' therefore can be produced by sexual reproduction by crossing 95265271× 95265026 to produce a population of progeny plants, each of which has the combination of characteristics as herein disclosed for the new cultivar. Seeds produced by crossing 95265271×95265026 have been deposited with the American Type Culture Collection, 10801 University Boulevard, Manassas, VA 20110-2209, and accorded Deposit Accession No. PTA-115. The seeds were deposited on May 24, 1999. The cultivar 'Primera' can also be produced by asexually reproducing progeny from the cross of 95265271×95265026 because the combination of characteristics as herein disclosed for the new cultivar 'Primera' are firmly fixed and are retained through successive generations of asexual reproduction.

OBJECTS OF THE INVENTION

This invention relates to seeds which produce *Aechmea fasciata* cultivar 'Primera'.

This invention also relates to *Aechmea fasciata* plants, and parts thereof, having all the physiological and morphological characteristics of *Aechmea fasciata* cultivar 'Primera'. This invention relates to a plant produced from seeds which are *Aechmea fasciata* cultivar 'Primera'. This invention also relates to plant parts, such as the pollen, seeds, or inflorescence, produced by *Aechmea fasciata* 'Primera'.

This invention relates to a method of producing seeds which are *Aechmea fasciata* cultivar 'Primera', by crossing *Aechmea fasciata* selection 95265271 as the female parent with *Aechmea fasciata* selection 95265026 as the male parent and the reciprocate cross with 95265026 as a female parent and 95265271 as a male parent and harvesting seeds produced from said crosses.

This invention also relates to a method of producing plants having all the physiological and morphological characteristics of the *Aechmea fasciata* cultivar 'Primera' comprising the steps of (a) crossing *Aechmea fasciata* selection 95265271 as the female parent with *Aechmea fasciata* selection 95265026 as the male parent; (b) harvesting seeds produced from said cross; and (c) producing plants from said harvested seeds.

BRIEF DESCRIPTION OF THE FIGURES

FIG. 1 shows a side view of a typical plant of 'Primera', with the colors being as true as possible with illustrations of this type.

DETAILED DESCRIPTION

This invention is directed to an *Aechmea fasciata* plant having all the morphological and physiological characteristics of the cultivar 'Primera' produced from seeds which are the product of the cross of *Aechmea fasciata* selection 95265271 as the female parent with *Aechmea fasciata* selection 95265026 as the male parent. Both parents have a sufficient degree of homozygosity such that the progeny of the cross were, and continue to be, phenotypically uniform. The variety 'Primera' therefore can be produced by sexual reproduction by crossing 95265271×95265026 to produce a population of progeny plants each of which has the combination of characteristics as herein disclosed for the new cultivar.

The variety 'Primera' can also be produced by asexually reproducing progeny from the cross of 95265271×95265026 because the combination of characteristics as herein disclosed for the new cultivar 'Primera' are firmly fixed and are retained through successive generations of asexual reproduction. The selection was first asexually propagated through offshoots by or under the supervision of the inventors in Assendelft, The Netherlands, with subsequent asexual reproduction being primarily by offshoots. Sexual and asexual propagation has demonstrated that the combination of characteristics as herein disclosed for the new cultivar 'Primera', as observed in Assendelft, The Netherlands, are firmly fixed and are retained through successive generations of asexual reproduction.

'Primera' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The following traits have been repeatedly observed and in combination distinguish 'Primera' as a new and distinct cultivar. These observations, measurements and descriptions were taken for 'Primera' plants grown under the following greenhouse conditions in Assendelft, The Netherlands. The minimum day and night temperature was 20 and 18° C., respectively. The ventilation temperature was 24° C. and the maximum light intensity was 18000 Lux. Fertilizer concentration was 0.5 to 1 EC comprising N:P:K in the ratio of 1:1:3 to 4 In addition, 3% of the total amount of fertilizer was MgS0$_4$. (15% MgO)

Frequency of fertilization varied depending on time of year and ranged from once per week to once per month. Fertilization was more frequent during the spring and summer months. Following fertilization, the plants were rinsed with sufficient clean water to remove residual fertilizer from the leaves. If fertilization frequency, or the concentration of fertilizer, is increased, 'Primera' leaves are darker in color, eventually resulting in burning of leaves and roots. If fertilization frequency, or the concentration of fertilizer, is decreased, 'Primera' leaves are lighter in color. If the ratio of N:K is increased above the value given above, 'Primera' leaves become darker in color, longer and more narrow. If the ratio of N:K is decreased below the value given above, 'Primera' leaves become lighter in color, shorter and broader. The intensity of the color of the inflorescence depends also on the amount of P.

With regard to induction of flowering, acetylene gas is allowed to bubble through 100 L of cool water for 30 min at a pressure of 0.5 bar. Whole plants are then sprayed with the acetylene solution making certain that the cup (vase) is filled. Spraying is done in the morning because the plants need light after this treatment and the plants are not watered again for at least two days. The plants are treated again, following this same protocol, one week later. The plants should not be fertilized for two to three weeks following treatment with acetylene because it is likely the flowers would not form and the bracts would remain green. The description of the new cultivar 'Primera' reported herein is based on measurements and observations of plants grown from seeds.

The following traits have been repeatedly observed to be characteristics which, in combination, distinguish *Aechmea fasciata* 'Primera' from the closest comparison cultivar, *Aechmea fasciata* 'Morgana'. The leaves of 'Primera' are spineless and dark greyed-green (RHS 189A) with whitish scales. The plant habit of 'Primera' is funnel-formed and rosette in shape.

I. Plant

The plant is funnel-form rosette in shape with a height of approximately 50 cm including inflorescence. The plant is stemless and measures approximately 50 cm in diameter.

II. Foliage

The leaves measure approximately 40–50 cm in length and approximately 8–14 cm in width. The shape of the leaf is broadly obovate and not narrowed at base. The leaves are arched and slightly recurving. The leaf sheath is ample, slightly contracted into the blade, broadly obovate, not inflated and approximately 12–14 cm wide. The color of the leaves are dark greyed-green (RHS 189A) with transverse white bands and patches. Most significantly, 'Primera' leaves do not have spines.

III. Inflorescence

A. Bracts:

The bracts are approximately 12 cm in length and approximately 2.5 cm wide. Each plant has approximately 40 bracts which are lanceolate in shape. The margin of each bract is entire. The primary bract color is RHTS 66D. The bracts are fasciculately compound and polystichously arranged. The bracts are very dense and the fertile part is approximately 10 cm long, and excluding involucral bracts, approximately 12 cm wide. The rachis is hidden and much reduced. The scape-bracts are sub-erect and recurving to form a rosette measuring over 25 cm in diameter. The floral-bracts are sub-erect and very densely imbricate, broadly ovate to ovate, and entire.

B. Flowers

The flowers of 'Primera' are sessile with a short and flat receptacle. The sepals are strongly asymmetric with a wing extending on left apex. The flowers are incurved toward the apex and approximately 1.2 cm long and 1 cm wide. The petals are free from each other, approximately 3.0 cm long and 0.6 cm wide. Ligules are present on the petals (claw). The exposed parts of the petals are violet-blue (RHS 98A) at the margins, fading to purplish-red, and lighter toward center. The anthers are dorsifixed, linear-sagittate and approximately 6.5 mm long. There are 6 anthers per flower. The stigmas are lobed and clasped in a spiral. The stamens are slightly longer than the pistil. The ovary is inferior and approximately 4 mm long. The filaments are slightly flattened toward the base and unequal. The filaments in the outer whorl are strongly curved (S-shaped) at the base. The anthers on one level are approximately 1.8 to 2 cm long and the inner whorl are adnate to the petals.

Mature 'Primera' plants bloom approximately 11 weeks after induction (natural or acetylene). Each flower blooms for about 1 day and the total length of blooming of the plant following induction is approximately 4 weeks.

C. Seed Characteristics

'Primera' is a sterile hybrid and therefore no fruit or seeds are produced by this cultivar.

We claim:

1. A seed which is *Aechmea fasciata* cultivar 'Primera' and accorded ATCC Deposit Accession No. PTA-115.

2. An *Aechmea fasciata* plant designated cultivar 'Primera' produced from seed accorded ATCC Deposit Accession No. PTA-115.

3. The pollen produced by the plant according to claim 2.

4. The inflorescence produced by the plant according to claim 2.

5. A method for producing an *Aechmea fasciata* plant comprising the steps of (a) crossing *Aechmea fasciata* cultivar 'Primera' produced from seed accorded ATCC Deposit Accession No. PTA-115 with another *Aechmea fasciata* plant and (b) selecting progeny.

* * * * *